United States Patent
Groswasser (10) Patent No.: US 8,605,282 B2
(45) Date of Patent: Dec. 10, 2013

(54) METHOD AND APPARATUS FOR HIGH PRECISION SPECTROSCOPY

(75) Inventor: David Groswasser, Ramat-Gan (IL)

(73) Assignee: Ben-Gurion University of the Negev Research and Development Authority, Beer-Sheva (IL)

( * ) Notice: Subject to any disclaimer, the term of this patent is extended or adjusted under 35 U.S.C. 154(b) by 19 days.

(21) Appl. No.: 13/319,177

(22) PCT Filed: May 6, 2010

(86) PCT No.: PCT/IL2010/000369
§ 371 (c)(1),
(2), (4) Date: Jan. 20, 2012

(87) PCT Pub. No.: WO2010/128513
PCT Pub. Date: Nov. 11, 2010

(65) Prior Publication Data
US 2012/0113423 A1 May 10, 2012

Related U.S. Application Data

(60) Provisional application No. 61/213,130, filed on May 8, 2009, provisional application No. 61/289,413, filed on Dec. 23, 2009.

(51) Int. Cl.
*G01J 4/00* (2006.01)
(52) U.S. Cl.
USPC .......................................... 356/367
(58) Field of Classification Search
USPC .......................................... 356/367
See application file for complete search history.

(56) References Cited

U.S. PATENT DOCUMENTS

| | | | |
|---|---|---|---|
| 3,742,382 A | 6/1973 | Smith et al. | |
| 5,054,921 A | 10/1991 | Hannaford et al. | |
| 6,477,189 B1 | 11/2002 | Takeda et al. | |
| 7,488,940 B2 * | 2/2009 | Ohtake et al. | 250/341.3 |
| 8,017,920 B2 * | 9/2011 | Suzuki et al. | 250/423 R |

OTHER PUBLICATIONS

Harris et al, "Polarization spectroscopy in rubidium and cesium", Physical Review A (Atomic, Molecular, and Optical Physics), The American Physical Society through AIP USA, vol. 73, No. 6, pp. 062509-1 to 062509-8 (2006).
Demtroder, Laser Spectroscopy, vol. 2, Technology, pp. 93-104 (2008).
Wieman and Hansch, "Doppler-Free Laser Polarization Spectroscopy", Physical Review Letters, vol. 36, No. 20, pp. 1170-1173 (May 1976).

(Continued)

*Primary Examiner* — Tu Nguyen
(74) *Attorney, Agent, or Firm* — Browdy and Neimark, PLLC (57) ABSTRACT

The invention provides spectroscopy apparatuses and methods allowing precise overlapping between circularly polarized pump beam and a counter propagating linearly polarized probe beams in a sample which presents unique advantages for precision spectroscopy. In general, the apparatus comprises a phase retarding element with which by double pass by retro reflection of an incident beam turn linearly polarized light to circular and vice versa. This unique configuration enable to design a compact and miniature apparatus which may be applied for measuring polarization spectroscopy, non-linear optical rotation and coherent population trapping phenomena with certain advantages resulting from the unique optical arrangement. The design of the apparatus further facilitates integration and scaling to produce arrays of units which may be particularly useful for magnetometry applications. Other important applications of the invention include laser frequency stabilization and atomic clocks.

28 Claims, 5 Drawing Sheets

(56) References Cited

OTHER PUBLICATIONS

Do et al, "Polarization Spectroscopy of Rubidium Atoms: Theory and Experiment," Physical Review A (Atomic, Molecular, and optical physics) The American Physical Society through AIP USA, vol. 77, No. 6, pp. 032513-1 to 032513-6 (2008).

Knappe, "Microfabricated saturated absorption laser spectrometer," Optics Express 20070514 Optical Society of America, U.S., vol. 15, No. 10, pp. 6293-6299 (May 14, 2007).

* cited by examiner

METHOD AND APPARATUS FOR HIGH PRECISION SPECTROSCOPY

FIELD OF THE INVENTION

The present invention relates to high precision spectroscopy, and more particularly to a method and apparatus utilizing polarization spectroscopy, nonlinear magneto optical rotation and coherent population trapping for detecting Doppler-free spectral features with high precision.

BACKGROUND OF THE INVENTION

In high precision spectroscopy measurements the Doppler broadening (spectral lines broadening due to velocity distribution of the particles) is a problem resulting in wide transition line shapes, which are usually too broad and thus not suitable for precision measurements. In order to resolve the naturally narrow spectral features that are hindered by this broad profile it is common to use a spectroscopy configuration employing two counter propagating laser beams.

Polarization spectroscopy is a known Doppler-free experimental technique utilized in high precision spectroscopy. It was first demonstrated by Wieman and Hänsch in 1976 [Wieman and Hänsch, "*Doppler-Free Laser Polarization Spectroscopy*" Phys. Rev. Lett. 36, 1170, (1976)]. The method is based on analysis of the rotation of the polarization plane of a probe laser beam which is passed through an optically polarized sample by a counter-propagating pump beam [Harris et al., "*Polarization spectroscopy in rubidium and cesium*". Phys. Rev. A 73, 062509, (2006)][Do et al., "*Polarization spectroscopy of rubidium atoms: Theory and experiment*", Phys. Rev. A 77, 032513 (2008)].

This technique is somewhat analogous to "Saturation spectroscopy" [Demtröder, "*Laser Spectroscopy*", (Springer, Berlin 1998)].

In polarization spectroscopy the pump beam is circularly polarized. This circularly polarized pump beam polarizes the sample, resulting in induced anisotropy. The counter-propagating probe beam, which is linearly polarized, travel through the polarized medium in an opposite direction. The change in the angle of the polarization plane of the probe beam due to passage through the polarized sample is analyzed by means of a polarimeter. As the laser frequency is scanned, the Doppler-free spectral features appear as very sharp error signals resulting from the dispersive-like nature of the phenomenon. The better the overlap between the two beams, the sharper the slope of the error signals.

Doppler-free polarization spectroscopy is often used for laser-locking. The main advantages of polarization spectroscopy for laser-locking are that the error signals are produced "naturally" as the laser frequency is scanned over the spectral range of the transitions. This is an advantage compared to saturation spectroscopy, that requires modulating the laser light and which requires additional electronic instruments such as a lock-in amplifier for generating the required error signals.

Figure 1:
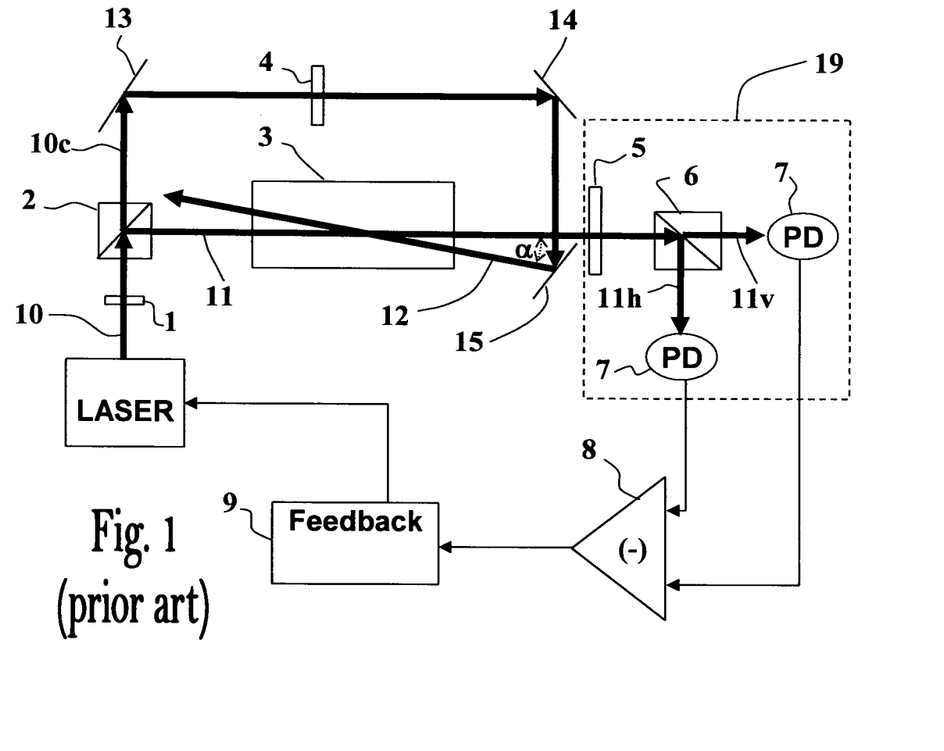
FIG. 1 schematically illustrates a prior art polarization spectroscopy configuration as typically implemented in laser frequency locking applications employing electronic feedback means adapted to adjust the laser frequency according to the error signals obtained.

A conventional setup for Doppler-free polarization spectroscopy is depicted in FIG. 1. In this prior art configuration, the power of the input laser beam 10 is divided into two beams by means of $\lambda/2$ waveplate 1 and a polarizing beam splitter cube (PBS—polarizing beam splitter) 2, which splits the beam entering into it into its vertical and horizontal linear polarization components. One component 11 is the probe beam which is reflected by PBS 2 to the sample cell 3. The other linear component 10c of input laser beam 10 is transmitted through PBS 2 and acquires a circular polarization by passing through the $\lambda/4$ waveplate 4 to become the pump beam 12. The probe beam 11 passes through the sample cell 3, and the pump beam 12 is directed by mirrors 13 14 and 15 to the opposite side of the sample cell 3 to nearly overlap the counter propagating probe beam 11.

The pump beam 12 polarizes the sample cell 3 and the rotation of the polarization plane of the probe beam 11 due to passing through the polarized sample is analyzed by a polarimeter 19. Polarimeter 19 may comprise a $\lambda/2$ waveplate 5 and a PBS 6 which splits the probe beam 11, which becomes circularly polarized as it passes through the $\lambda/2$ waveplate 5, into its vertical and horizontal linear polarization components, 11v and 11h. Vertical and horizontal linear polarization components 11v and 11h are then measured by means photodetectors 7.

In polarization spectroscopy the difference between the signals measured by the two photodetectors 7 is amplified by differential amplifier 8 and is measured as a function of the frequency of input laser beam 10. The spectral features of this technique are commonly used as error signals that can serve as input for a feedback system 9 used for locking the laser frequency.

In this configuration the sample atoms which interacts with both the pump and the probe laser beams are only the atoms which do not have velocity components in the direction of propagation of the pump and probe beams, 12 and 11. It is therefore desirous that the pump and probe beams substantially overlap in order to cancel Doppler broadening components. However, as seen in FIG. 1, the pump and probe beams nearly overlap, and inherently, it is not possible to perfectly overlap the pump and probe beams in such conventional polarization spectroscopy setups since there will always be an angle of $\alpha$ degrees between them, which spoils measurements precision.

U.S. Pat. Nos. 3,742,382 and 5,054,921, describe similar Doppler-free configurations. These prior art Doppler-free configurations do not enable perfect overlap between the pump beam and the probe beam. As will be appreciated by those skilled in the art, in order to reduce the angle $\alpha$ between the pump and the probe beams and increase the beam overlap, it is required to extend the length of such conventional Doppler-free configurations and therefore to increase the dimensions of the apparatus. Such a configuration is not ideal for miniaturization and alignment. Additional difficulties arising in such conventional spectroscopy setups are due to the multiple mirror elements comprised therein that require careful alignment, and thus complicates the assembly of devices based on it.

Polarization spectroscopy configuration can also be used to measure magnetic fields with high accuracy using a phenomenon commonly known as Nonlinear Magneto Optical Rotation (NMOR) [Budker and Romalis, "*Optical Magnetometry*" Nature Physics, 3, 227 (2007)][Budker et al., "*Resonant nonlinear magneto-optical effects in atoms*", Reviews of Modern Physics, 74, 1153 (2002)]. In NMOR, the medium is spin polarized due to the difference between absorption coefficients (circular dichroism) of the left and right circular polarization components. The medium dichroism causes the polarization of the probe beam to become elliptical, and the optical birefringence ($\Delta n = n_+ - n_-$, where $n_+$ and $n_-$ are the refractive indices for right and left circular polarizations) induces the rotation of the axis of polarization of the linearly polarized probe beam by $\Delta\theta = \Delta n k_0 L/2$, where $k_0$ is the wave number of the probe beam, L is the length of the sample cell, and $\Delta n$ is the optical birefringence. Accordingly, the magnitude of magnetic fields can be detected and accurately measured by exposing the sample (i.e., atomic vapor) to the magnetic field to be measured.

On-resonance NMOR detection causes excitation of the medium and changes the properties of the state to be measured. Therefore the most sensitive up-to-date magnetometers use a probe beam that is detuned far from the resonance frequency. Off-resonance detection is compatible with high probe-beam intensities, which improve the signal-to-noise ratio. NMOR is also often operated in a pump-probe configuration [Kominis et al., "*A subfemtotesla Multichannel atomic magnetometer*", Nature, 422, 596 (2003)], as in polarization spectroscopy. In such NMOR setups the pump beam polarizes the sample and the resulting magnetization process around the direction of the magnetic field and is detected by the probe beam. However, in most cases where NMOR is performed in a pump-probe fashion the beams are perpendicular to each other [Kominis et al., Nature, 422, 596 (2003)], hence the sensitivity is limited by the intersection volume of the beams. Furthermore, in the common pump-probe NMOR setups, in which the beams are perpendicular to each other, it is necessary to have optical access to the vapor cell from two directions which present a difficulty when considering scalability in applications requiring array of such pump-probe NMOR cells (e.g., magnetic imaging).

Coherent Population Trapping (CPT) is a known resonance phenomenon occurring due to a quantum mechanical interference effect in an atomic/molecular system that cancels the absorption of a coherent bichromatic light field [Wynands and Nagel, "*Precision spectroscopy with coherent dark states*" Appl. Phys. B 68, 1-25 (1999)]. The bichromatic light field is comprised of two phase coherent optical frequencies, and wherein the frequency difference between these two fields matches the ground state splitting in the sample there is a change in the intensity of the light transmitted through the sample. This change is strongly dependent on the frequency difference between the two phase coherent fields. CPT proved to be useful for various application in areas as diverse as laser cooling [Metcalf and der Straten, "*Laser cooling and trapping of atoms*" J. Opt. Soc. Am. B 20, 887 (2003)], frequency standards [Vamier, "*Atomic clocks based on coherent population trapping: a review*", Appl. Phys. B 81, 421, (2005)] [Vanier et al., "*Coherent population trapping in cesium: Dark lines and coherent microwave emission*" Phys. Rev. A 58, 2345 (1998)], high-sensitivity optical magnetometry [Nagel et al., "*Experimental realization of coherent dark-state magnetometers*", Europhys. Lett., 44, 31-36 (1998)][Schwindt et al., "*Chip scale atomic magnetometer*" Appl. Phys. Lett. 85, 6409 (2004)] and light storage [Phillips et al., "*Storage of light in atomic vapor*" Phys. Rev. Lett. 86, 783-786 (2001)]. In many cases the term Electromagnetic Induced Transparency (EIT) is used to describe the same phenomenon. It is also important to note that in most cases, CPT signals are weak (reduce the absorption signal by ~1-2%) due to radiative decay of the atomic population to "extreme" states which are not coupled with the two phase coherent light fields, which are often called trapped states.

CPT is commonly applied on a sample cell containing a vapor of alkali metal. In general, the ground state hyperfine splitting in alkali atoms is in the microwave range (~6.8 GHz in Rb, 9.2 GHz in Cs). To produce two coherent light fields with such a frequency difference it is common to modulate the laser current with a microwave source. Coherent population trapping (CPT), has applications in areas as diverse as laser cooling frequency standards and high-sensitivity magnetometry.

For completeness, the accuracy of the above mentioned spectroscopy techniques depends on the coherence lifetime of the atoms which in practice is reduced by a variety of nonradiative processes such as atom-atom collisions or collisions with the vapor cell walls. Hence, to reduce the decoherence rate of these processes the vapor cell inner walls are sometimes coated by a substance such as paraffin which maintains the spin coherence of the atoms even after many collisions. To reduce decoherence rate due to collisions between alkali atoms, often the cell is filled with high pressure inert gas such as He, Ar etc.

The approaches described above do not provide satisfactory solutions for high precision Doppler-free spectroscopy. Therefore there is a need for improved precision Doppler-free spectroscopy configurations.

One object of the present invention is to provide high precision Doppler-free polarization spectroscopy configurations suitable to be used as atomic references.

It is also an object of the present invention to provide high precision Doppler-free polarization spectroscopy configurations in which Doppler-broadening effects are substantially minimized or even entirely cancelled.

It is another object of the present invention to provide a method and apparatus for high precision Doppler-free polarization spectroscopy allowing for significant miniaturization of the apparatus, and that can also be used for magnetometry applications.

It is a further object of the present invention to provide a method and apparatus for optically pumped magneto optical rotation magnetometer with improved optical access.

It is yet a further object of the present invention to provide a method and apparatus for high precision Doppler-free polarization spectroscopy that allows combining laser locking with CPT measurements.

An additional object of the present invention is to provide a method and an apparatus for improving the contrast of a CPT signal.

Other objects and advantages of the invention will become apparent as the description proceeds.

SUMMARY OF THE INVENTION

The present invention provides a methods and apparatuses for Doppler-free polarization spectroscopy, that enables perfect pump-probe beams overlap, and that substantially miniaturize the apparatus geometrical dimensions. The Doppler-free polarization spectroscopy apparatuses of the invention can be further utilized to measure magnetic fields intensities using NMOR, and with some modifications to measure CPT signals with relatively improved contrast.

The present invention provides a method and apparatus for significantly improving pump-probe beams overlap in polarization spectroscopy. In general, the method comprises directing an input laser beam towards a sample contained in a gas cell (also referred to herein as a sample cell or vapor cell) and retro-reflecting it back on itself as in Doppler-free saturation spectroscopy. However, in the present invention, one of the two counter propagating beams has a circular polarization component that is used to optically pump and polarize the sample, while the other beam has a linear polarization component that is used for the probing of the sample as a function of the laser frequency. Polarization spectroscopy is often used on-resonance to lock the laser frequency to an atomic transition line. However, the same optical configuration can be applied for detecting and measuring magnetic fields, even if the laser frequency is tuned off-resonance by employing conventional NMOR techniques including lock-in detection

[Acosta et al., "*Nonlinear Magneto-optical rotation with frequency-modulated light in the geophysical field range*", Phys. Rev. A 73, 053404 (2006)]. The terms retro-reflected beam and counter propagating beam used herein to refer to a beam of light reflected by optical reflection means in 180° to the incident beam, or in other words, the incident beam is reflected back on itself, such that the reflected beam substantially propagates in the same path of the incident beam, but in the opposite direction. The term overlapping beams used herein to refer to beams propagating in the same path in space, and in particular, to a retro-reflected beam propagating through cross-sectional areas in space which are comprised in, or the same as, the cross-sectional areas of the incident beam. The terms waveplate and optical retarding element used herein to refer to optical devices that alters the polarization of light beams traveling through them.

According to one preferred embodiment of the invention, also referred to herein as the "T" configuration, the input laser beam is directed by a non-polarizing element such as a non-polarizing beam-splitter cube (NPBS) for passage thorough the sample cell, said beam is circularly or elliptically polarized before passing through the sample cell in order to optically pump anisotropy in the sample. Alternatively, the input laser beam may be produced by a laser source adapted to provide a circularly or elliptically polarized laser beam.

The passage of the circularly or elliptically polarized beam (referred to herein as pump beam) through the sample cell (e.g. Rb vapor cell) induces anisotropy of the sample. Following the passage through the sample cell, said pump beam passes through a polarizer such as a linear polarizer or through a phase retarding element, such as a $\lambda/8$ waveplate, or a $\lambda/4$ waveplate. The pump beam is then retro-reflected back towards the sample cell by means of optical reflecting means (e.g., mirror), and it may optionally be attenuated before reaching the mirror by optical or electrooptical means such as filters or by using optical reflecting means having partial reflectance features (e.g., partial reflection mirror). Accordingly, the direction of the retro-reflected beam is 180° relative to the probe beam passed through the sample cell. The retro-reflected beam is passed through the attenuator and the polarizing or phase retarding element so that its intensity is optimized and its polarization becomes linear or elliptically polarized before it is passed through the sample cell in a direction opposite to the direction of the pump beam, such that the retro-reflected (returning) beam (referred to herein as probe beam) is overlapping the counter-propagating pump beam. The anisotropy and optical dichroism/birefringence in the sample induced by said pump beam, causes a rotation of the polarization plane of the probe beam passed through the sample cell, which is analyzed by means of a polarimeter.

In one specific preferred embodiment of the invention, the "T" configuration apparatuses may comprise a light coupling input port, an optically non-polarizing splitting element, such as NPBS cube, capable of directing an input laser beam passed through the light coupling port towards the sample cell, a $\lambda/4$ waveplate for obtaining a pump beam by circularly or elliptically polarizing said input laser beam, a magnetically shielding container (e.g. such as mu metal) comprising said sample cell, a phase retarding element such as a $\lambda/8$ waveplate, $\lambda/4$ waveplate, or a polarizing element, such as a linear polarizer, employed for obtaining a probe beam with linear polarization component, and for varying the angle of the polarization plane of said linear component in order to balance the polarimeter, a filter (placed between the sample cell and the mirror) for attenuating the probe beam intensity, a mirror (which can be semi-transparent and is preferably placed behind the filter and the phase retarding or polarizing element) for retro-reflecting said probe beam, such that it is caused to pass again through said polarizing or phase retarding element on its return to the sample cell in 180° direction relative to the pump beam, and a polarimeter for measuring the angle of rotation of the polarization plane of the retro reflected light. The polarimeter is placed behind the optically non-polarizing splitting element opposite to the sample cell; it preferably comprises a polarizing beam-splitter cube (PBS), two photodetectors and a differential amplifier for amplifying the difference between the output signals of said two photodetectors. Preferably, the light coupling input port is implemented by an optical fiber, or through air.

This preferred embodiment may be easily modified to further allow measurement of CPT signals by employing a frequency modulated laser beam as the input beam, and by implementing the optical reflecting means by means of a semi-transparent mirror, thereby allowing a fraction of the intensity of the beam hitting it to pass through it in the direction of a third photodetector placed therebehind and adapted for CPT signals measurements (CPT measurements by absorbance). Alternatively or additionally, an additional photodetector may be positioned adjacent the vapor cell containing the sample and adapted for fluorescence detection for coherent population trapping measurements (CPT measurements by fluorescence).

According to another preferred embodiment of the invention, also referred to herein as the "linear" configuration, the input beam is linearly polarized and provides the probe beam as it passes through the sample cell. After exiting the sample cell, this beam acquires a circular polarization component by passing through a first phase retarding element, such as a $\lambda/8$ waveplate. Thereafter, a portion of this beam is retro-reflected towards the sample cell by a semi-transparent mirror in order to optically pump it. The retro-reflected beam is thus in a direction being 180° relative to the probe beam i.e., the probe beam and the retro-reflected beam are overlapping. The retro-reflected beam is passed through the same phase retarding element (i.e., the first phase retarding element), but this time in a direction opposite to that of the probe beam.

Due to the double pass of the beam through phase retarding element (first pass in the probe beam and second pass in the retro-reflected beam) it acquires circular (or elliptical) polarization, hence providing the pump beam. The elliptically polarized beam passed through the semi-transparent mirror retrieves its linear polarization by passing through a second phase retarding element which is configured to cancel the effect of the first phase retarding element. For example, the two phase retarding elements may be implemented by means of $\lambda/8$ waveplates. The optical axes of these two waveplates are preferably rotated by 90° one relative to the other in order to allow the second phase retarding element to cancel the effects induced in the probe beam by the first phase retarding element. The anisotropy and optical dichroism/birefringence in the sample induced by said pump beam, causes a rotation of the polarization plane of the passing probe beam which is analyzed by means of a polarimeter.

This preferred embodiment may be easily modified to further allow measurement of CPT signals by employing a linearly polarized and frequency modulated laser beam as the input beam and adding an optical beam splitter, such as a PBS, between the laser and the sample cell in order to direct a fraction of the beam after its passage through the sample cell towards a photo-detector. Alternatively or additionally, an additional photodetector may be positioned adjacent the sample cell and adapted for fluorescence detection for coherent population trapping measurements (CPT measurements by fluorescence).

In one specific preferred embodiment of the invention, the "linear" configuration apparatus may comprise a light coupling input port configured to direct an input laser beam for passage through the sample cell, a magnetically shielded container (e.g. such as mu metal) comprising the sample cell, a first phase retarding element such as a λ/8 waveplate that is situated behind the sample cell (i.e., opposite to the side facing the light coupling input port), and a semi-transparent mirror situated behind said first phase retarding element. Said first phase retarding element is configured to circularly or elliptically polarize the reflected light from the semi-transparent mirror due to the double passage through it (i.e., first passage in the probe beam and second passage in the retro-reflected beam), hence providing the pump beam. The semi-transparent mirror is employed for reflecting part of the light towards the sample cell in the 180° direction relative to the probe beam, to optically polarize it and to transmit part of the light passed through it for analysis of the optical activity in the sample. This apparatus also comprises a second phase retarding element that is placed behind the semi-transparent mirror. Said second phase retarding element may be identical to the first phase retarding element that is placed between the sample cell and the semi-transparent mirror. Said second phase retarding element is employed for canceling the effect of said first phase retarding optical element in the part of the light passed through the semi-transparent mirror. For example, said two phase retarding elements may be implemented by two λ/8 waveplates which have their optical axes rotated by 90 degrees in respect to each other. The apparatus also comprises a polarimeter preferably including a polarizing beam-splitter cube (PBS), two photodetectors and an amplifier for amplifying the difference between outputs of said photodetectors. Preferably, the light coupling input port is implemented by an optical fiber, or through air.

According to another aspect, the present invention is directed to the miniaturization of a Doppler-free polarization spectroscopy apparatus that enables perfect pump-probe beams overlap.

Preferably, when used for laser locking or as a frequency standard the apparatus is magnetically shielded, temperature stabilized and vibrationaly isolated. However, in magnetometer implementations of the invention there is no need for magnetic isolation and therefore the vapor cell containing the sample and any housing in which the apparatus may be enclosed should not comprise any magnetic shielding in order to allow the measurement of the magnetic influences.

In one aspect the present invention is directed to a spectroscopy apparatus comprising a vapor cell comprising a reference atomic or molecular vapor medium, optical means adapted for receiving an input beam of light and for producing by retro reflection means a pump beam and a probe beam, wherein the pump and probe beams are overlapping and counter propagating and pass through said vapor cell, and polarimetery means adapted to receive said probe beam following its passage through said vapor cell for providing indications regarding polarization plane angle of its linearly polarized component, wherein said pump beam comprises a circularly polarized component and said probe beam is linearly polarized.

According to one preferred embodiment of the invention the input beam of light is substantially parallel to the probe and pump beams. The input beam of light in this preferred embodiment is preferably a linearly polarized laser beam that is used as the probe beam, such that the apparatus is adapted to receive the input beam of light and pass it through the vapor cell and thereafter through the optical means in direction of the polarimeter means. The optical means are disposed between the vapor cell and the polarimeter means and comprises two phase retarding elements each capable of canceling retardation effects of the other (e.g., a λ/8 waveplate set at −45° and another λ/8 waveplate set at +45°), and a semi transparent optical reflection element (e.g., semi-transparent mirror) placed between the two phase retarding element.

In this way portion of the beam received in the optical means after passage through the vapor cell is reflected back towards the vapor cell through a first phase retarding elements (i.e., the phase retarding element disposed between the vapor cell and the semi transparent optical reflection element). The double trip through the first phase retarding element (first passage in the beam arriving from the vapor cell and second passage in the reflected beam) circularly polarizes the retro reflected pump beam. The portion of the incident beam that passes through the semi transparent optical reflection element towards the polarimeter passes through the second phase retarding element (i.e., the phase retarding element disposed between the semi transparent optical reflection element and the polarimeter), which cancels phase retardations induced by the first phase retarding element, which thus becomes linearly polarized. The polarimeter signal may be applied for laser frequency lock or for measuring NMOR signals.

Advantageously, the two phase retarding elements and the semi transparent optical reflection element are arranged as a single integrated optical unit. Preferably, the two phase retarding elements are λ/8 waveplates and the semi transparent optical reflection element is implemented by a semi transparent mirror. Alternatively, the semi transparent optical reflection element may be implemented by a type of a semi reflecting coating applied on one of the phase retarding elements.

The apparatus may be further used for coherent population trapping measurements by using a frequency modulated laser beam as the input beam of light, and by using a photodetector and an optical beam splitting means for directing a portion of the pump beam passed through the vapor cell in direction of the photodetector for the coherent population trapping measurements. Additionally or alternatively, coherent population trapping measurements may be carried out by means of a photodetector positioned adjacent the vapor cell and adapted for fluorescence detection.

According to another preferred embodiment the input beam of light is substantially perpendicular to the probe and pump beams. In this preferred embodiment the optical means may comprise optical phase retarding means and non-polarizing beam splitting means adapted to add a circularly polarized component to the input beam of light and direct a portion thereof to be used as the pump beam for passage through the vapor cell, optical or electro-optical phase retarding means and optical reflecting means adapted to receive a beam obtained from the passage of said pump beam through the vapor cell, produce a linearly polarize beam, and direct the linearly polarize beam to be used as the probe beam for passage through the vapor cell. Advantageously, the apparatus may further comprise optical attenuation means adapted for attenuating the reflected beam before its passage through the vapor cell. Preferably, the optical phase retarding means is implemented by a λ/4 waveplate and the optical or electro-optical phase retarding means is implemented by a λ/8 waveplate. Preferably, the optical reflecting means is a mirror or a semi transparent mirror.

According to one specific preferred embodiment of the invention, the optical phase retarding means is disposed between the optical non-polarizing beam splitting means and the vapor cell, and in this case the apparatus further comprises an additional optic phase retarding element (e.g., a λ/4 waveplate) adapted for canceling the circular polarization of the probe beam before it reaches the polarimeter means.

The apparatus may be further used for coherent population trapping measurements by using a frequency modulated laser beam as the input beam of light, a semi transparent mirror and a photodetector for measuring absorption of the pump beam after it is passed through the vapor cell for the coherent population trapping detection. Additionally or alternatively, coherent population trapping measurements may be carried out by means of a photodetector positioned adjacent the vapor cell and adapted for fluorescence detection. The apparatus of the invention may be further used for measuring magnetic fields. Additionally or alternatively, the apparatus of the invention may be used as an atomic reference (frequency standard). According to yet another specific preferred embodiment of the invention the apparatus of the invention may be employed for laser frequency stabilization by polarization spectroscopy.

Advantageously, the polarization spectroscopy configurations of the present invention may be used to assemble an array of apparatuses (e.g., based on the "linear" configuration apparatus), this array of apparatuses is particularly suitable for magnetic sensing (e.g., magnetic imaging) due to gradiometry and common mode noise rejection capabilities. Such an array of apparatuses may be assembled from multiple vapor cells or alternatively share a single large vapor cell. The array may also share a single integrated component made of semi-transparent reflection means sandwiched between two optical phase retarding elements (as in the "linear" configuration of the invention). This integrated component may be attached to one side of the array of cells (or alternatively single large vapor cell) while on the other side of the array of cells (or single large cell) there is placed an array of polarimetery units adapted to measure polarization plane angles of the probe beams. The input beam to the array may be provided by an array of lasers, i.e., a single laser unit per each polarimetery unit, or by a single laser with an expanded output beam.

According to another aspect the present invention is directed to a method for carrying out high precision spectroscopy measurements, the method comprising receiving a beam of light, producing from the beam of light by means of optical reflecting means and optical retarding means a pump beam comprising a circularly polarized component and an overlapping and counter propagating linearly polarized probe beam, passing the pump beam and the probe beam through a vapor cell comprising a sample, and measuring the polarization plane angle of the probe beam after its passage through the sample.

According to one preferred embodiment of the invention the received beam of light is substantially parallel to the probe and pump beams. According to another preferred embodiment of the invention the received beam of light is substantially perpendicular to the probe and pump beams. The method may further comprise measuring coherent population trapping by using a frequency modulated laser beam as the input beam of light, and by measuring fluorescence emitted from the vapor cell, for example, by means of a photodetector. Alternatively or additionally, the measuring of coherent population trapping may be carried out by measuring absorption, either by directing a portion of the pump beam after its passage through the vapor cell to photo-detecting means as in the linear configuration, or by photodetection of the pump beam portion that passed through the semi transparent mirror as in the "T" configuration of the current invention. The method may be further adapted for measuring magnetic fields, for laser frequency stabilization, and/or for atomic frequency standards.

According to yet another aspect the present invention is directed to an integrated unit of optical means capable of receiving a linearly polarized beam of light and producing a counter propagating beam having a linear polarization and a circular polarization, this integrated unit comprises two phase retarding elements and a semi transparent reflection element sandwiched between the two phase retarding elements, wherein each one of the two phase retarding elements is configured to cancel retardation effects induced by the other. In this way a portion of the received linearly polarized beam of light introduced into the integrated unit through one of the phase retarding elements is retro-reflected by the semi-transparent reflection element and passed through the same phase retarding element and become circularly polarized, while the portion of the received beam passing through the semi-transparent reflection element passes through the other phase retarding element and thus becomes linearly polarized.

Other objects and details of the invention will be clear and apparent from the following detailed description, in which reference is made to the following drawings, in which specific embodiments of the invention are shown.

BRIEF DESCRIPTION OF THE DRAWINGS

The present invention is illustrated by way of example in the accompanying drawings, in which similar references consistently indicate similar elements and in which:

FIGS. 2A and 2B schematically illustrate "T" shaped retro-reflecting polarization spectroscopy embodiments of the invention in which the laser beam is frequency modulated to produce two phase coherent fields, wherein

FIGS. 3A and 3B schematically illustrates linear configuration of a retro-reflecting polarization spectroscopy apparatus of the invention in which the laser beam is frequency modulated to produce two phase coherent fields, wherein

FIGS. 4A to 4E graphically illustrates comparison between spectra of the $5S_{1/2}, F=2 \rightarrow 5P_{3/2}, F'=2$ D2 transition in $^{87}Rb$, wherein FIGS. 5A to 5C schematically illustrates various embodiments of an array of retro-reflecting polarization spectroscopy apparatuses of the invention, wherein

It is noted that the embodiments exemplified in the Figs. are not intended to be in scale and are in diagram form to facilitate ease of understanding and description.

DETAILED DESCRIPTION OF PREFERRED EMBODIMENTS

The present invention provides a method and apparatus for retro-reflecting Doppler-free polarization spectroscopy, enabling substantially improved overlapping of pump and probe beams, improved precision of the measured signals, and miniaturization of the apparatus. The present invention further provides optical polarization spectroscopy setups suitable for measuring magnetic fields by NMOR and for CPT measurements.

Figure 2A:
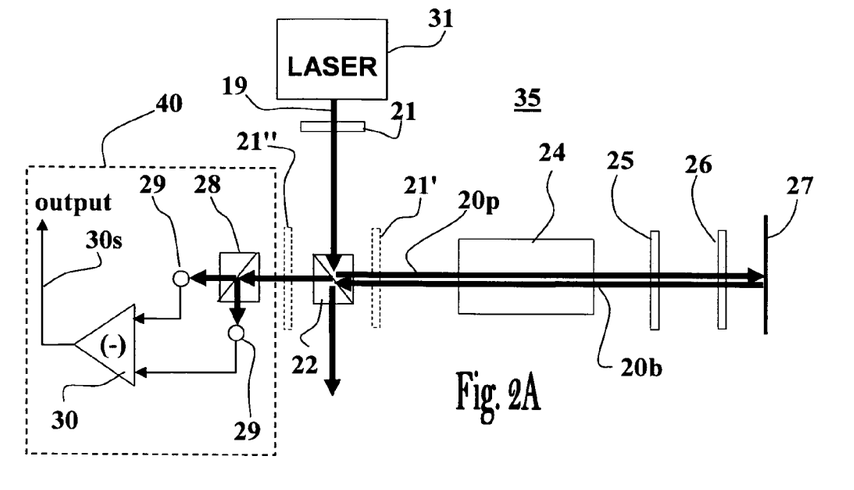
FIG. 2A illustrates a "T" shaped embodiment for polarization spectroscopy measurements.

With reference to FIG. 2A, showing an optical arrangement of apparatus 35 of the invention, also referred to hereinafter as the "T" shape configuration, comprising an input light beam 19 provided by a laser source 31 which is conventionally capable of producing a linearly polarized laser beam. The apparatus 35 includes a phase retarding element 21 used for circularly or elliptically polarizing the input beam 19. Apparatus 35 also includes a non-polarizing splitting element 22 (e.g., NPBS—non-polarizing beam splitter), enabling directing portion of the beam entering it towards the sample cell 24. Phase retarding element 21 may be placed between laser source 31 and non-polarizing splitting element 22, or alternatively, between non-polarizing splitting element 22 and sample cell 24 (21' indicated by dashed line), such that the pump beam 20p obtained from it is circularly or elliptically polarized before it enters the sample cell 24. Thus it should be clear that in case phase retarding element 21' is used in apparatus 35 i.e., it is disposed between NPBS 22 and sample cell 24, as demonstrated in FIG. 2A, then the phase retarding element 21 placed in front of laser source 31 is removed from apparatus 35.

Apparatus 35 comprises a sample cell 24 provided in a container (not shown), an optical or electro-optical element and an optical filter 26 which are placed between the sample cell 24 and mirror 27 which is used to retro-reflect the light to the sample cell 24. Optical or electro-optical element 25 is used for linearly polarizing the retro-reflected light, such that probe beam 20b has a linear polarization component before it enters sample cell 24. Filter 26 is used for attenuating the optical intensity of probe beam 20b.

Apparatus 35 further comprises a polarimeter 40 utilized for analyzing the rotation of the polarization plane of the probe beam 20b due to the passage through the polarized sample in sample cell 24. The polarimeter 40 consists of a polarizing-beam-splitter-cube 28, two photodetectors 29 and a differential amplifier 30, which receives the outputs from the photodetectors 29 and produces an electrical output signal 30s.

If the phase retarding element 21' is placed between non-polarizing element 22 and sample cell 24 (i.e., instead of having phase retarding element 21 placed between laser source 31 and NPBS 22), the probe beam 20b will be passed through it before reaching polarimeter 40 and thus will acquire a circular polarization. In this case, it is necessary to insert phase retarding element 21" (indicated by dashed lines), between the NPBS 22 and PBS 28 in order to retrieve the linear polarization component of probe beam 20b.

The input beam 19 (conventionally a linearly polarized laser beam) may be coupled into the apparatus through air, or by means of optical fibers. The intensity of input beam 19 and its polarization can be optimized to get the best results by conventional methods before or after it enters the apparatus 35.

After the coupling of the input beam 19 into apparatus 35 it is necessary to circularly or elliptically polarize the input beam 19 before it enters the sample cell 24. Therefore, the input beam 19 is passed through a phase retarding element 21 which is preferably a $\lambda/4$ waveplate and is directed by the non-polarizing splitting element 22, which is preferably a conventional non-polarizing beam-splitter cube towards the sample cell 24. Alternatively, the input beam 19 is first directed by the non-polarizing element 22 towards the sample cell 24 and it is then passed through a phase retarding element 21' which is preferably a $\lambda/4$ waveplate. In both alternatives the result is a pump beam 20p having circular or elliptical polarization before entering the sample cell 24. The pump beam 20p polarizes the sample contained in sample cell 24 as it passes through it. An example of a suitable sample cell is a glass cell containing vapor of alkali atoms.

The pump beam 20p exit sample cell 24 and passes through the optical element 25, which has two functions: (a) ensuring that the polarization of the retro-reflected probe beam 20b has a linear polarization component on return to the sample cell 24; and (b) rotating the polarization plane of the probe beam 20b in order to balance (calibrate) the polarimeter 40 such that the electrical output signal is zeroed if no polarization is induced in sample contained in sample cell 24 by pump beam 20p. Optical element 25 is preferably a conventional $\lambda/8$, waveplate, or another suitable phase retarding element, such as a $\lambda/4$, waveplate which is applied in case wherein the pump beam 20p is elliptically polarized. It is noted that the intensity losses in the beams due to the passage through element 25 are substantially small.

Alternatively, optical element 25 may be implemented by a polarizer, such as a linear polarizer, capable of transmitting only one linear component of the polarization. In this case the beam intensity will drop when it is passed through this polarizing element. After passing through optical element 25 the beam travels toward an optional attenuator 26 employed for attenuating the intensity of the probe beam 20b if required. Attenuator 26 may be implemented by an absorption filter, or by means of a certain coating applied on mirror 27. The attenuated beam obtained after the passage through attenuator 26 is retro-reflected by mirror 27 towards the sample cell 24, so that following the return pass through optical element 25 the probe beam 20b, acquires a linear polarization component.

In the sample cell, the probe beam 20b overlaps the counter-propagating pump beam 20p. Optical dichroism and birefringence effects causes rotation in the polarization plane of probe beam 20b as it passes through the optically polarized sample in sample cell 24. The probe beam 20b continues out from the sample cell 24, and the spectral features are embedded in the angle of the polarization plane. After exiting sample cell 24, probe beam 20b passes through non-polarizing element 22, before reaching the polarimeter 40 for analysis.

Of course, if phase retarding element 21' is used instead of phase retarding element 21, then probe beam is further passed through phase retarding elements 21' and 21", before reaching polarimeter 40. As explained above, phase retarding element 21" is used in this alternative embodiment for canceling the circular polarization applied to probe beam 20b by phase retarding element 21', and thereby to allow polarimeter 40 to detect rotations in its polarization plane. Phase retarding element 21" may be implemented by a $\lambda/4$ waveplate placed before polarimeter 40, as demonstrated in FIG. 2A. The advantage of this alternative embodiment is that all the optical elements in the apparatus are parallel and its assembly is relatively simple and easy, however, it requires one additional optical element 21". Of course, if phase retarding element 21 is used between laser source 31 and NPBS 22, elements 21' and 21" are not required in apparatus 35 and are removed therefrom.

The rotation of the angle of the polarization plane of the probe beam 20b is analyzed by a polarimeter 40 which is used for measuring the rotation of the polarization plane of the probe beam, and which comprises a polarizing beam splitter cube 28, and two photodetectors 29 (e.g. photodiodes). A differential amplifier 30 is used for amplifying the difference between the output signals received from the two photodetectors 29. The polarimeter 40 is balanced off resonance, such that the signals received from the photodetectors 29 cancel each other, but as the frequency of laser beam 19 is tuned closer to the resonance frequency of the sample in sample cell 24, there is a change in the angle of the polarization plane of the linear polarization component of the probe beam 20b, and non-zero readings are then obtained from the polarimeter 40.

The optical elements including waveplates, non-polarizing beam splitter, mirror, PBS and filter, employed in apparatus 35 are preferably similar to the conventional elements used in spectroscopy applications, but preferably have reduced geometrical dimensions (miniaturized). While the sample may be placed in a conventional glass cell with some alkali vapor, it is preferably contained in a container having substantially reduced geometrical dimensions, which may be manufactured, for example, as described in Knappe and Liew [Knappe et al., "*Atomic vapor cells for chip-scale atomic clocks with improved long-term frequency stability*", Opt. Lett. 30, 2351 (2005)][Liew et al., "Microfabricated alkali, atom vapor cells", Appl. Phys. Lett. 84, 2694 (2004)].

Figure 2B:
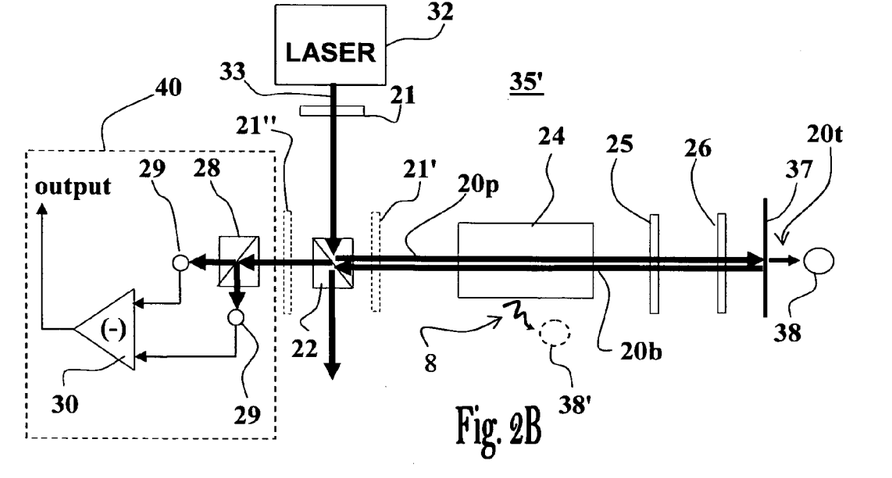
FIG. 2B illustrates an embodiment in which following the passage through the sample cell the circularly polarized beam is partially transmitted through a semi-transparent mirror towards a photodetector used for detecting CPT resonance.

With reference to FIG. 2B, showing a modification of the "T"-shaped configuration allowing CPT measurements in addition to the polarization spectroscopy measurement described above. As seen, apparatus 35' in this preferred embodiment is substantially similar to apparatus 35 depicted in FIG. 2A, but with the following changes:

laser beam 33 provided by laser source 32 is frequency modulated and is composed of two phase coherent optical fields; and in order to allow CPT measurements by absorbance of the laser beam a semi transparent mirror 37 is used in this embodiment, such that portion 20t of the beam reaching semi transparent mirror 37 is passed through it and measured by means of photodetector 38.

Optionally photodetector 38' (indicated by a broken line) may be located adjacent to the sample cell 24 for measuring the CPT by detecting the fluorescence 8 emitted from the sample contained in sample cell 24, which is proportional to the absorbance.

Figure 3A:
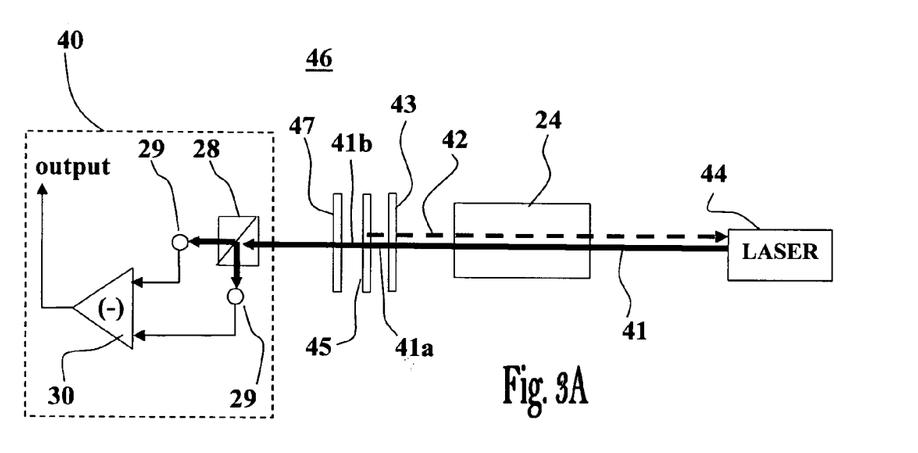
FIG. 3A illustrates a linear configuration for polarization spectroscopy measurements.

FIG. 3A schematically illustrates apparatus 46 exemplifying another preferred retro-reflecting polarization spectroscopy embodiment of the invention of the invention, also referred to herein as the "linear" configuration. Apparatus 46 comprises a laser source 44, a sample contained in sample cell 24, three optical or electrooptical elements 43, 45 and 47, and polarimeter 40. In this configuration the linearly polarized probe beam 41 provided by laser source 44 is passed through sample cell 24 and through optical, or electrooptical, elements 43, 45 and 47 placed along its path between sample cell 24 and polarimeter 40.

Optical or electrooptical elements 43, 45 and 47, which may be manufactured as a single integrated unit comprising the three functional elements, are adapted for providing a circularly polarized pump beam 42 that is reflected back therefrom towards sample cell 24, and for allowing passage of portion 41b of the input probe beam 41 towards polarimeter 40, with the needed linear polarization (i.e., such that the output from polarimeter 40 is zeroed whenever no anisotropy is induced in the sample contained in sample cell 24).

According to one preferred embodiment the first optical or electrooptical phase retarding element 43 is a $\lambda/8$ waveplate set at 45° with respect to the polarization axis of the input probe beam 41, the second electrooptical element 45 is a semi-transparent mirror having reflectivity of about 1% to 99% preferably about 90% (high sensitivity detectors at the polarimeter 40 will enable higher reflectivity), and the third optical or electrooptical phase retarding element 47 is also a $\lambda/8$ waveplate set at −45° with respect to the polarization axis of the input probe beam 41. In this way the linearly polarized input probe beam 41 forwardly passing through the first phase retarding optical or electrooptical element 43 ($\lambda/8$ at 45° obtains a circular polarization component 41a, and the portion thereof which is backwardly reflected by semi-transparent mirror 45 (i.e., from which pump beam 42 is obtained) becomes elliptically or completely circularly polarized following the return pass through first optical or electrooptical phase retarding element 43. This pump beam 42, continue to pass through sample cell 24, counter propagating and overlapping the probe beam 41. The portion 41b of the elliptically polarized beam 41a that is transmitted through the semi-transparent mirror 45 is passed through the third optical or electrooptical phase retarding element 47 ($\lambda/8$ at −45° which reverse the retardation effect of element 43 hence retrieving the linear polarization state of the input probe beam 41 before reaching the polarimeter 40 for analysis of any rotations in the polarization angle of the probe beam 41 induced by optical activity in the sample cell 24.

Figure 3B:
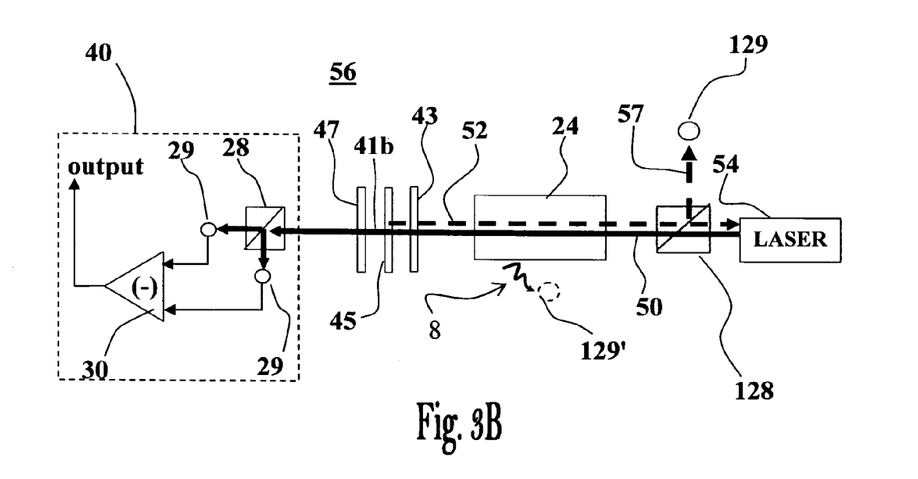
FIG. 3B illustrates a configuration in which following the passage through the sample cell the circularly polarized retro-reflected beam is reflected by a polarizing cube towards a photodetector to detect the CPT resonance.

FIG. 3B schematically illustrates an apparatus 56 exemplifying a modification of the "linear" retro-reflecting polarization spectroscopy configuration of the invention (46 shown in FIG. 3A) allowing both polarization spectroscopy and CPT measurements. Apparatus 56 comprises a laser source 54, a sample contained in a sample cell 24, three optical or electrooptical elements 43 45 and 47, and polarimeter 40. In this configuration the input beam from the laser source 54 is passed through a PBS 128, the linearly polarized probe beam 50 is frequency modulated, and is passed through sample cell 24 and through the optical or electro-optical elements 43, 45 and 47 placed along its path between sample cell 24 and polarimeter 40, as described with reference to FIG. 3A. The frequency modulated and circularly polarized retro reflected pump beam 52 is passed through the sample cell 24 and hits the PBS 128 which reflect part of it 57 towards a photodetector 129 which is used for CPT analysis.

Optionally photodetector 129' (indicated by a broken line) may be located adjacent to the sample cell 24 for measuring the CPT by detecting the fluorescence 8 emitted from sample contained in sample cell 24, which is proportional to the absorbance.

The polarization spectroscopy signals are very important for many applications where a laser with extremely narrow spectral linewidth is needed (e.g. for laser cooling of Rb atoms, typically a linewidth of less than 1 MHz is required). In this case, the resulting error signals from the apparatus can serve as a precise input reference frequency for a feedback system for locking laser frequency [Pearman et al., "*Polarization spectroscopy of a closed atomic transition: applications to laser frequency locking*", J. Phys. B: At. Mol. Opt. Phys. 35, 5141 (2002)][Yoshikawa et al., "*Frequency stabi-* lization of a laser diode with use of light-induced birefringence in an atomic vapor" Appl. Opt. 42, 6645 (2003)][Groswasser et al., "*Retroreflecting polarization spectroscopy enabling miniaturization*", Rev. Sci. Inst. 80, 093103 (2009)]. An example for such a system is a P-I-D controller. Finally, the spectral linewidth of a given laser system is determined by the intrinsic stability of the laser and by isolating from external disturbances. In alkali atoms the optical transitions are typically few MHz wide due to the lifetime of the excited states. The laser is locked to the atomic reference frequency as long as the electronic feedback system manages to keep the laser frequency within this range. See [Groswasser et al., "*Retroreflecting polarization spectroscopy enabling miniaturization*", Rev. Sci. Inst. 80, 093103 (2009)].

The CPT signals are important for precise measurements such as in atomic clocks and magnetometers. The modified apparatuses 35' and 56 of the invention (shown in FIGS. 2B and 3B) are particularly advantageous, inter alia, as they combine possible laser locking implementations together with CPT measurement in the same apparatus. Furthermore, it is suggested that the forward propagating linearly polarized probe beam can optically pump back "lost" atomic population from the trapped states and return it to the lambda system [Phillips et al., Phys. Rev. Lett. 86, 783-786 (2001)][Watabe et al., "*High-contrast dark resonances with linearly polarized light on the Dl line of alkali atoms with large nuclear spin*" Appl. Opt. 48, 1098 (2008)], hence improving the contrast of the CPT signal.

For laser locking and frequency standards (e.g., atomic clocks) applications, the performance of the apparatuses of the invention may be improved by applying vibration isolation, temperature stabilization, and magnetic shield, all of which are within the skills of persons having ordinary skill in the art. The frequency shifts of the spectral features in this technique are very sensitive for external disturbances, more specifically to magnetic fields, hence the apparatus, or part of the apparatus which includes the sample should be magnetically shielded. For example the magnetic shielding can be implemented by a type of the so-called mu-metal case.

On the other hand, the magnetic sensitivity of the apparatuses of the present invention may be employed for magnetic field measurements, and in such implementations the sample cell 24 should be exposed to the measured magnetic field, and accordingly in this case there is no need to apply any type of magnetic shielding means.

Figure 4A:
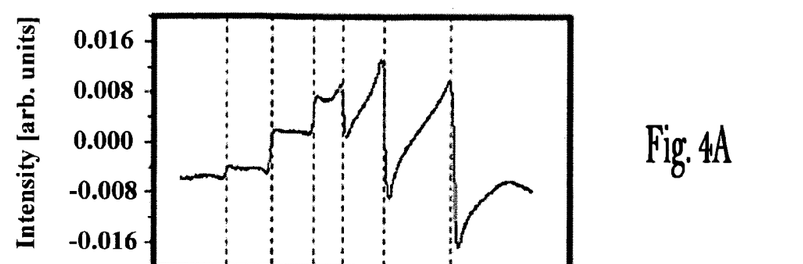
FIG. 4A shows the spectra obtained with the "T"-shape polarization spectroscopy configurations of the invention.
Figure 4B:
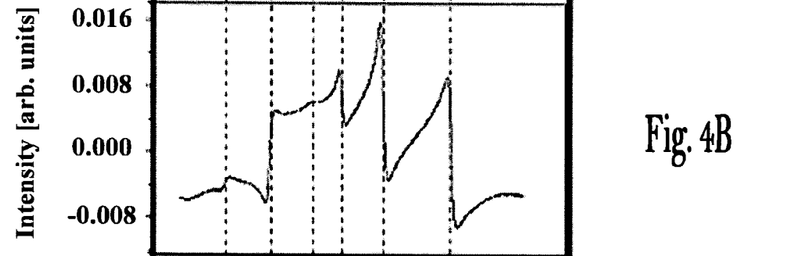
FIG. 4B shows the spectra obtained with a $\lambda/8$ waveplate.
Figure 4C:
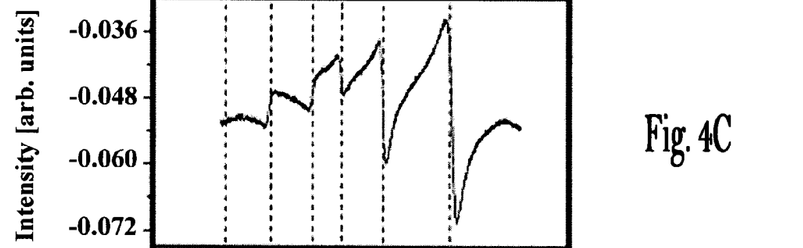
FIG. 4C shows the spectra obtained with the linear configuration of the invention.
Figure 4D:
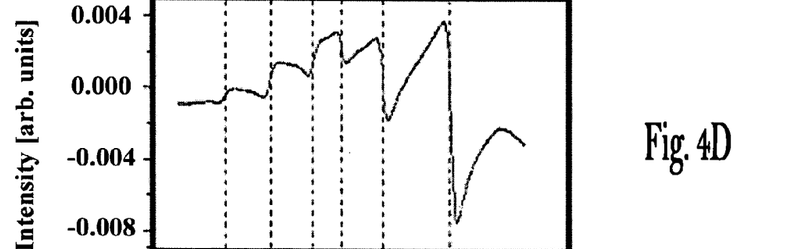
FIG. 4D shows the spectra obtained with standard polarization spectroscopy.
Figure 4E:
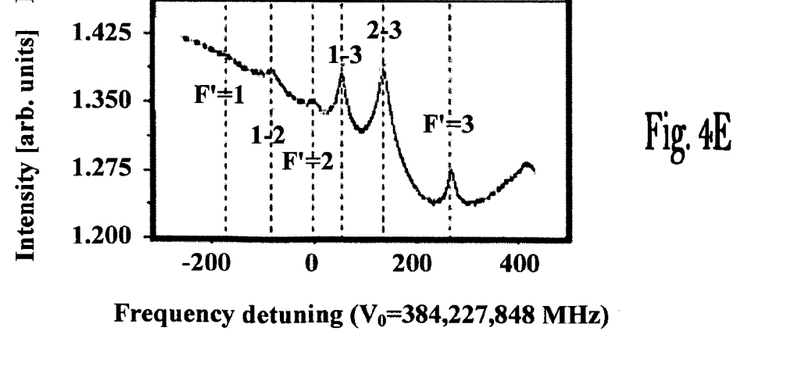
FIG. 4E shows the spectra obtained with a Doppler-free saturation spectroscopy for reference.

FIGS. 4A to 4E show the polarization spectroscopy results obtain with the invention as published in [Groswasser et al., "*Retroreflecting polarization spectroscopy enabling miniaturization*", Rev. Sci. Inst. 80, 093103 (2009)]. More particularly, FIGS. 4A to 4E graphically illustrates comparison between spectra of the $5S_{1/2}$, F=2→$5P_{3/2}$,F'=2 D2 transition in $^{87}$Rb, wherein FIG. 4A shows the spectra obtained with the "T"-shape polarization spectroscopy configurations of the invention 35 shown in FIG. 2A (employing phase retarding element 21) in which optical element 25 is a linear polarizer, FIG. 4B shows the spectra obtained with "T" configuration 35 in which element 25 is a λ/8 waveplate. FIG. 4C shows the spectra obtained with the linear configuration of the invention (shown in FIG. 3A), FIG. 4D shows the spectra obtained with standard polarization spectroscopy (e.g., shown in FIG. 1), and FIG. 4E shows the spectra obtained with a Doppler-free saturation spectroscopy for reference.

With today's state-of-the-art technology, the dimensions of conventional Doppler-free polarization spectroscopy apparatuses are limited by the size of the sample cell and surrounding optical elements. For estimation, the volume of the "Chip Scale Atomic Magnetometer" which is a similar device that includes a miniature vapor cell is only 12 mm$^3$ [Wynands and Nagel, Appl. Phys. B 68, 1-25 (1999)]. However, in implementations wherein standard vapor cell are used the dimensions of the device will be greater and can take a volume of about 15000 cm$^3$.

In most cases wherein NMOR is performed in a pump-probe fashion the beams are perpendicular to each other, hence the sensitivity is limited by the intersection volume of the beams. In the configurations of the present invention this volume is limited only by the length of the sample cell containing the sample, which may be advantageously employed for miniaturization purposes.

Improving the contrast of CPT signals is the topic of several research works [Watabe et al., Appl. Opt. 48, 1098 (2008)][Shah et al., "*High-contrast coherent population trapping resonances using four-wave mixing in 87Rb*" Opt. Lett. 32, 1244 (2007)]. As will be appreciated by those skilled in the art the retro reflecting optical configuration of the present invention improves the contrast of this signal by using a counter propagating linearly polarized beam that excites atoms that are in the extreme trapped states back into states which are coupled by the circularly polarized phase coherent beams.

Figure 5A:
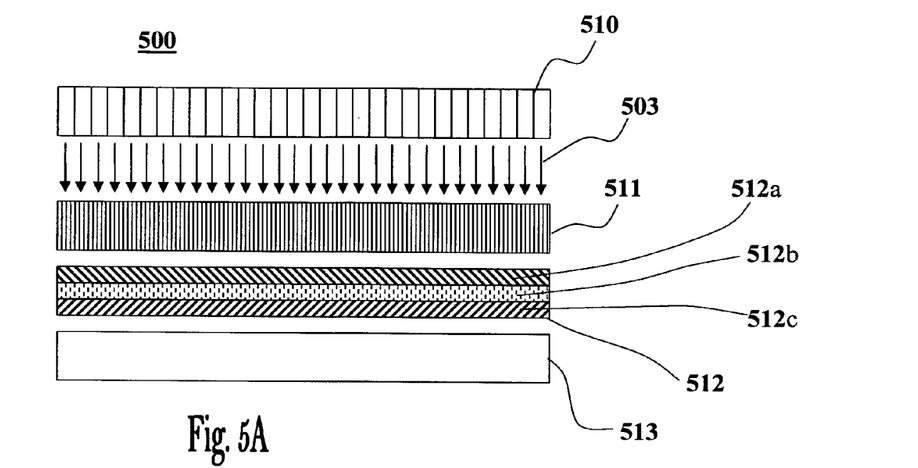
FIG. 5A illustrates an embodiment comprising an array of lasers sources.
Figures 5B, 5C:
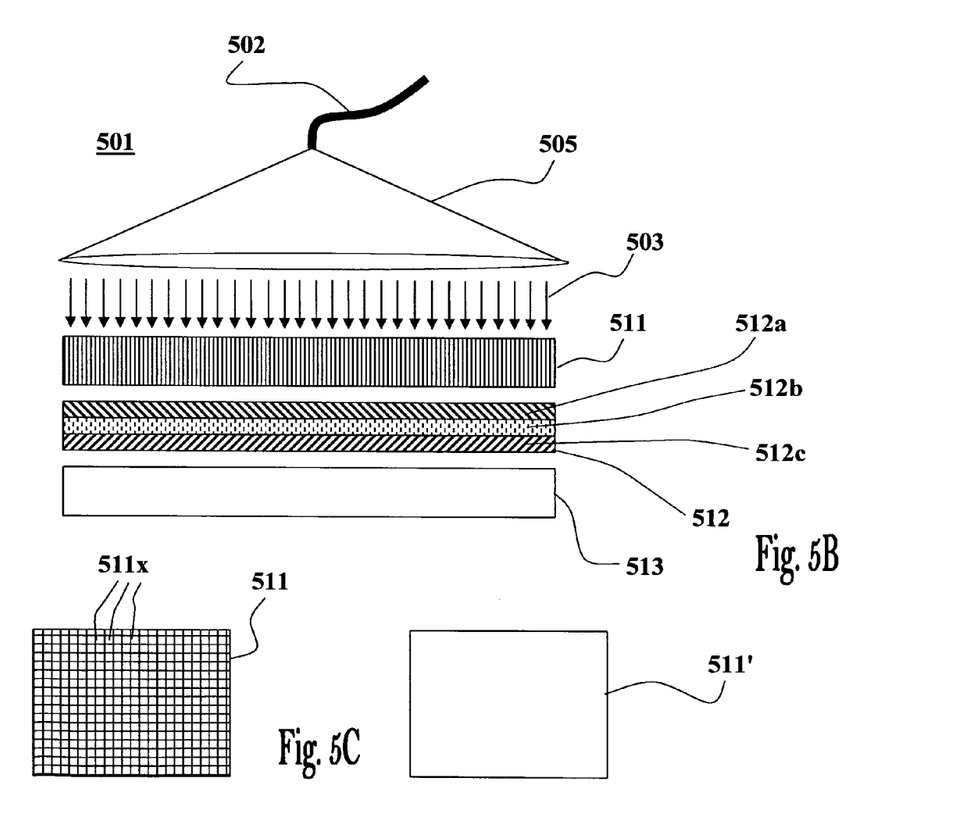
FIG. 5B illustrates and embodiment comprising a single laser source and a beam expander.
FIG. 5C illustrates (not in scale) employing a single vapor cell, or alternatively an array of vapor cells.

Furthermore, as shown in FIGS. 4A-4C, the resulting spectral features obtained with the configurations of the present invention can be used as error signals which are particularly advantageous for laser-locking. Furthermore, the apparatuses of the present invention can be integrated in laser systems, for reducing the spectral linewidth of the laser. Additionally, as described in details hereinabove, the apparatuses of the present invention can be easily modified to enable measuring coherent population trapping (CPT) signals. The applications for such optical systems may include, inter alia, laser cooling, slow light and light storage, atomic clocks, optical magnetometers, optical communication and more. FIGS. 5A to 5C schematically illustrates various embodiments of an array of retro-reflecting polarization spectroscopy apparatuses based on the linear configuration of the invention suitable for magnetic sensing (e.g., magnetic imaging) due to gradiometry and common mode noise rejection capabilities.

FIG. 5A illustrates an array 500 of retro-reflecting polarization spectroscopy apparatuses comprising an array of lasers sources 510, a corresponding array of vapor cells 511, an integrated optical means unit 512 comprising two phase retarding elements 512a and 512c and a semi-transparent reflection element 512b sandwiched between them, and an array of polarimetry units 513. In this embodiment beams of linearly polarized laser light 503 are emitted towards the vapor cells array 511 (made of cell units 511x in FIG. 5C), or alternatively a single large vapor cell (511' in FIG. 5C). A portion of laser light transmitted through the vapor cell array 511 (or large vapor cell 511') is retro reflected from the semi transparent element 512b which is sandwiched between two phase retarding elements 512a and 512c. Elements 512a, 512b and 512c may be integrated in a single optical means unit 512. Each of the phase retarding elements 512a and 512c in the integrated optical means unit 512 is configured to cancel phase retardation induced by the other phase retarding element in the unit. The integrated optical means unit 512 is adapted to produce a circularly polarized beam retro-reflected towards the array of vapor cells 511 (or alternatively the single large cell 511') and a linearly polarized beam propagating towards the polarimetry array 513, as in the "linear" configuration of the invention described with reference to FIG. 3A.

FIG. 5B illustrates an embodiment 501 of the array of retro-reflecting polarization spectroscopy apparatuses shown in FIG. 5A employing a single laser source that is transferred through a beam expander 505. In this example the input beam is a linearly polarized laser beam introduced into beam expander 505 via an optical fiber 502.

As shown in FIG. 5C (not in scale), the array of vapor cells 511 may be implemented employing a plurality of vapor cells 511x, or alternatively, instead of using a plurality of vapor cells, a large single vapor cell 511' may be used common to all polarimetry units in the polarimetry units array 513.

The above examples and description have of course been provided only for the purpose of illustration, and are not intended to limit the invention in any way. As will be appreciated by the skilled person, the invention can be carried out in a great variety of ways, employing more than one technique from those described above, all without exceeding the scope of the invention.

The invention claimed is:

1. A spectroscopy apparatus comprising:
a vapor cell comprising a reference atomic or molecular vapor medium;
optical means adapted for receiving an input beam of light and for producing by retro reflection means a pump beam and a probe beam, said pump and probe beams are overlapping and counter propagating and pass through said vapor cell; and
polarimeter means adapted to receive said probe beam following its passage through said vapor cell for providing indications regarding polarization plane angle of its linearly polarized component,
wherein said pump beam comprises a circularly polarized component and said probe beam is linearly polarized.

2. The apparatus according to claim 1 wherein the input beam of light is substantially parallel to the probe and pump beams.

3. The apparatus according to claim 2 wherein the input beam of light is a linearly polarized laser beam that is used as a probe beam, and wherein said apparatus is adapted to receive said input beam of light and pass it through the vapor cell and thereafter through the optical means in direction of the polarimeter means, said optical means are disposed between said vapor cell and said polarimeter means and comprises two phase retarding elements, each capable of canceling retardation effects of the other, and a semi transparent reflection element placed between said two phase retarding elements such that the portion of the beam received in said optical means after passage through the vapor cell is retro reflected by said semi transparent reflection element and becomes circularly polarized, and the portion of the received beam transmitted through said semi transparent optical reflection element towards the polarimeter becomes linearly polarized.

4. The apparatus according to claim 3 wherein the two phase retarding elements and the semi transparent optical reflection element are arranged as a single integrated optical unit.

5. The apparatus according to claim 3 wherein the two phase retarding elements are $\lambda/8$ waveplates and the semi transparent optical reflection element is implemented by a semi transparent mirror or a type of a semi reflecting coating applied on one of said waveplates.

6. The apparatus according to claim 3, wherein the input beam of light is a frequency modulated laser beam, said apparatus further comprising a photodetector and optical beam splitting means adapted to direct a portion of the pump beam passed through the vapor cell in direction of said photodetector for coherent population trapping measurements.

7. An apparatus according to claim 6 used as frequency standard.

8. The apparatus according to claim 3, wherein the input beam of light is a frequency modulated laser beam, said apparatus further comprising a photodetector positioned adjacent the vapor cell and adapted for fluorescence detection for coherent population trapping measurements.

9. The apparatus according to claim 1 wherein the input beam of light is substantially perpendicular to the probe and pump beams.

10. The apparatus according to claim 9 wherein the optical means comprises:
optical phase retarding means and non-polarizing beam splitting means adapted to add a circularly polarized component to the input beam of light and direct a portion thereof to be used as the pump beam for passage through the vapor cell;
optical or electro-optical phase retarding means and optical reflecting means adapted to receive a beam obtained from the passage of said pump beam through said vapor cell, produce a linearly polarize beam, and direct said linearly polarized beam to be used as the probe beam for passage through said vapor cell.

11. The apparatus according to claim 10 further comprising optical attenuation means adapted for attenuating the reflected beam before its passage through the vapor cell.

12. The apparatus according to claim 10 wherein the optical phase retarding means is a $\lambda/4$ waveplate and the optical or electro-optical phase retarding means is a $\lambda/8$ waveplate.

13. The apparatus according to claim 10 wherein the optical phase retarding means is disposed between the optical non-polarizing beam splitting means and the vapor cell, further comprising an additional optic phase retarding means adapted to cancel circular polarization of the probe beam before it reaches the polarimeter means.

14. The apparatus according to claim 13 wherein the additional optic phase retarding means is a $\lambda/4$ waveplate.

15. The apparatus according to claim 9 wherein the input beam of light is a frequency modulated laser beam and the optical reflecting means is a semi-transparent mirror, said apparatus further comprises a photodetector adapted to receive a portion of the beam passed through said semi-transparent mirror for coherent population trapping measurements.

16. The apparatus according to claim 9, wherein the input beam of light is a frequency modulated laser beam, said apparatus further comprises a photodetector positioned adjacent the vapor cell and adapted for fluorescence detection for coherent population trapping measurements.

17. An apparatus according to claim 1 for measuring magnetic fields.

18. An apparatus according to claim 1 used for laser frequency stabilization by: polarization spectroscopy.

19. An array of apparatuses according to claim 1 for magnetometry measurements with gradiometry and substantial common mode noise rejection capabilities.

20. An array of apparatus according to claim 19 sharing a single vapor cell.

21. A method for carrying out high precision spectroscopy measurements, comprising:
receiving a beam of light;
producing from said beam of light by means of optical reflecting means and optical retarding means a pump beam comprising a circularly polarized component and an overlapping and counter propagating linearly polarized probe beam;

passing said pump and probe beams through a vapor cell comprising a sample; and measuring the polarization plane angle of said probe beam after its passage through said sample.

22. A method according to claim 21 wherein the received beam of light is substantially parallel to the probe and pump beams.

23. A method according to claim 21 wherein the received beam of light is substantially perpendicular to the probe and pump beams.

24. A method according to claim 21 wherein the input beam of light is a frequency modulated laser beam, further comprising measuring coherent population trapping by detection of fluorescence from the vapor cell.

25. The method according to claim 24 used for atomic frequency standards.

26. A method according to claim 21 wherein the input beam of light is a frequency modulated laser beam, further comprising photo-detecting means for measuring coherent population trapping by detecting the absorption of the pump beam following its passage through the vapor cell.

27. The method according to claim 21 for measuring magnetic fields.

28. The method according to claim 21 used for laser frequency stabilization.

* * * * *